(12) United States Patent
Hama et al.

(10) Patent No.: US 6,184,400 B1
(45) Date of Patent: *Feb. 6, 2001

(54) METHOD OF MANUFACTURING A FATTY ACID ESTER OF POLYOXYALKYLENE ALKYL ETHER

(75) Inventors: Ituo Hama; Takahiro Okamoto; Hisashi Sasamoto; Hirofumi Nakamura, all of Tokyo (JP)

(73) Assignee: Lion Corporation, Tokyo (JP)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/104,209

(22) Filed: Jun. 25, 1998

Related U.S. Application Data

(62) Division of application No. 08/629,068, filed on Apr. 8, 1996, now Pat. No. 5,817,844.

(51) Int. Cl.$^7$ .................................................. C07C 62/02
(52) U.S. Cl. .......................... 554/223; 544/224; 544/227; 560/224; 560/263
(58) Field of Search ..................................... 502/340, 341, 502/344, 346, 355; 554/223, 224, 227; 560/224, 263

(56) References Cited

U.S. PATENT DOCUMENTS

| | | | |
|---|---|---|---|
| 5,374,750 | * 12/1994 | Nakamura et al. | 554/149 |
| 5,741,947 | * 4/1998 | Wolf et al. | 568/618 |
| 5,750,796 | * 5/1998 | Hama et al. | 568/618 |

\* cited by examiner

*Primary Examiner*—Richard L. Raymond
(74) *Attorney, Agent, or Firm*—Bacon & Thomas

(57) ABSTRACT

A method of manufacturing a fatty acid ester of polyoxyalkylene alkyl ether wherein a fatty acid ester of polyoxyalkylene alkyl ether represented by the following formula (I) is produced through a reaction between a fatty acid alkyl ester with an alkylene oxide in the presence of a composite metal-oxide catalyst whose surface is modified with a metal hydroxide or a metal alkoxide:

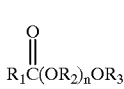

(I)

wherein each of $R_1$ and $R_3$ independently represents an alkyl group or an alkenyl group, $R_2$ represents an alkylene group, and n is a positive number.

8 Claims, 3 Drawing Sheets

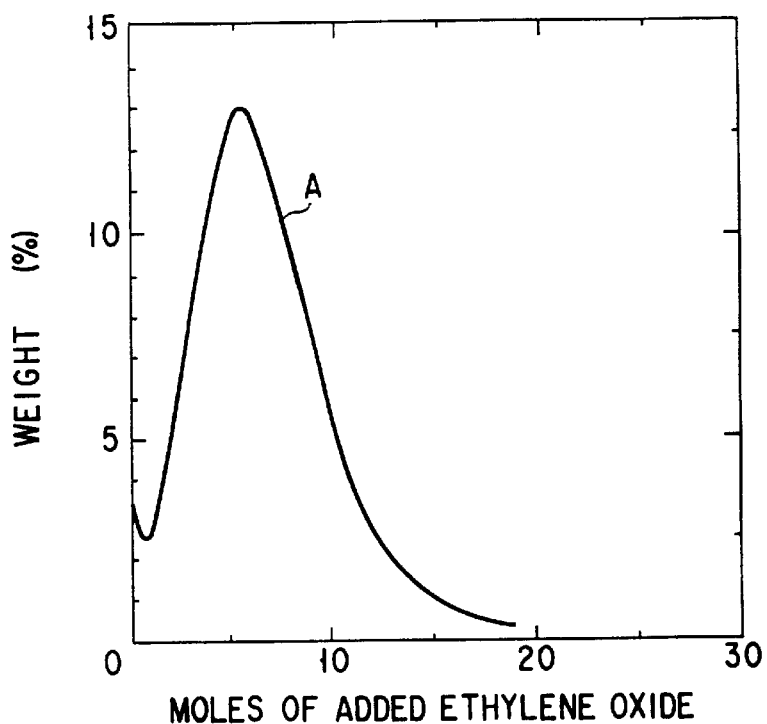
F I G. 1
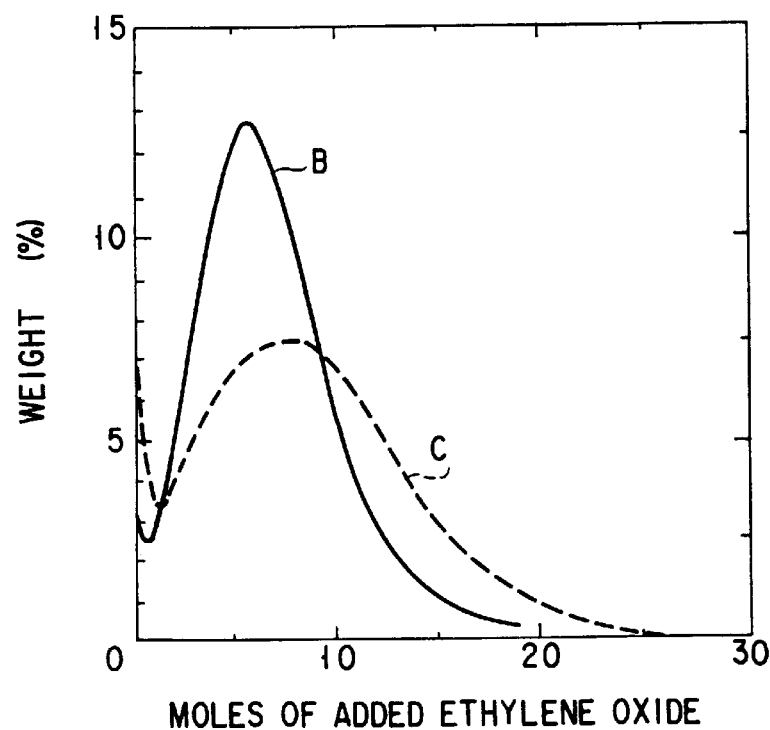
F I G. 2

METHOD OF MANUFACTURING A FATTY ACID ESTER OF POLYOXYALKYLENE ALKYL ETHER

CROSS REFERENCE TO RELATED APPLICATION

This application is a divisional application of application Ser. No. 08/629,068 filed Apr. 8, 1996, now U.S. Pat. No. 5,817,844.

BACKGROUND OF THE INVENTION

1. Field of the Invention

The present invention relates to a method of manufacturing a fatty acid ester of polyoxyalkylene alkyl ether having an alkylene oxide in an extremely narrow molar distribution, by directly reacting an fatty acid alkyl ester with an alkylene oxide using a surface-modified composite metal-oxide catalyst.

2. Description of the Related Art

Fatty acid esters of polyoxyalkylene alkyl ethers are known as ester-type nonionic surfactants. Of these, stearic polyoxyethylene stearyl ether represented by the following formula (1) is utilized as an emulsifier, a dispersant, or an oil-phase adjuster in the cosmetics field and in various industrial fields.

(1)

Polyoxyethylene methyl ether laurate represented by the following formula (2) has been investigated as to the possibility for use in a wetting agent (JAOCS, 56:873 (1979)).

(2)

Application of the fatty acid esters of polyoxyalkylene alkyl ethers to detergent compositions (Jpn. Pat. Appln. Nos. 3-229548, 3-321106), to deinking agents for use in a paper regeneration process (Jpn. Pat. Appln. No. 4-209010), or to others have been also expected.

A polyoxyethylene alkyl ether and a polyoxyethylene fatty acid ester, each to be used as a typical nonionic surfactant of an ethylene oxide adduct type, can be obtained by using an alcohol or a fatty acid as a starting material, and directly addition-polymerizing ethylene oxide and the staring material in the presence of an alkaline or an acidic catalyst.

In the case of obtaining a fatty acid ester of polyoxyalkylene alkyl ether, however, the addition polymerization reaction of an alkylene oxide does not proceed even if a fatty acid alkyl ester is allowed to react with an alkylene oxide in the presence of an alkaline or an acidic catalyst.

The methods of manufacturing a fatty acid ester of polyoxyalkylene alkyl ether by means of a one-step reaction between a fatty acid alkyl ester and an alkylene oxide are reported in the following publications:

1) Jpn. Pat. Appln. KOKAI Publication No. 56-36431: acetic acid ester of polyoxyalkylene alkyl ether is synthesized from an alkyl acetate and an alkylene oxide, using a calcined hydrotalcite compound as a catalyst.

2) Jpn. Pat. Appln. KOKOKU Publication No. 53-24930: a fatty acid ester of polyoxyalkylene alkyl ether is produced through a reaction between an alkylene oxide and an organic carboxylate by using a catalyst consisting of a halide of zinc, aluminum or the like, or consisting of an organometallic compound containing zinc or aluminum, or by using an alternative catalyst consisting of a combination of the aforementioned catalyst and an amine compound or the like.

3) Jpn. Pat. Appln. KOKAI Publication No. 54-1038125: acetic acid ester of polyoxyethylene ethyl ether is produced through a reaction between ethyl acetate and an excessive ethylene glycol monoethyl ether in the presence of a strong acidic cation exchange resin.

4) Jpn. Pat. Appln. KOKAI Publication No. 4-279552: a fatty acid ester of polyoxyalkylene alkyl ether is synthesized by means of a reaction between a fatty acid alkyl ester and an alkylene oxide, using a metal-ion (aluminum etc.) added magnesium oxide as a catalyst.

5) Jpn. Pat. Appln. KOKAI Publication No. 4-505449: a fatty acid ester is ethoxylated or propoxylated by using a calcined hydrotalcite as a catalyst.

As mentioned above, when a fatty acid alkyl ester is reacted with an alkylene oxide in the presence of a composite metal-oxide catalyst such as a metal-ion (aluminum etc.) added magnesium oxide or a calcined hydrotalcite, it is known that the alkylene oxide is added to the fatty acid alkyl ester in such a way that the alkylene oxide enters into an ester bond, resulting in a fatty acid ester of polyoxyalkylene alkyl ether.

The aforementioned methods are, however, not fully satisfactory from an industrial point of view due to three drawbacks. First, an alkylene oxide adduct distribution in a product is wide. Second, an unreactive fatty acid alkyl ester is remained in a large amount. Third, the product is colored.

SUMMARY OF THE INVENTION

An object of the present invention is to provide a method of manufacturing a fatty acid ester of polyoxyalkylene alkyl ether, which permit manufacturing a product having a narrow alkylene oxide adduct distribution and to reduce an amount of a remaining unreactive fatty acid alkyl ester.

Another object of the present invention is to provide a composite metal-oxide catalyst which is suitable for use in a method of manufacturing a fatty acid ester of polyoxyalkylene alkyl ether, which permit manufacturing a product having a narrow alkylene oxide adduct distribution and to reduce an amount of a remaining unreactive fatty acid alkyl ester.

According to the present invention, there is provided a method of manufacturing a fatty acid ester of polyoxyalkylene alkyl ether, which comprises reacting a fatty acid alkyl ester with an alkyl oxide in the presence of a composite metal-oxide catalyst whose surface is modified by a metal hydroxide or a metal alkoxide, thereby manufacturing a fatty acid alkyl ester of polyoxyalkylene alkyl ether represented by the following formula (I):

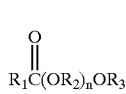
(I)

wherein each of $R_1$ and $R_3$ independently represents an alkyl group or an alkenyl group, $R_2$ represents an alkylene group, and n is a positive number.

Further, according to the present invention, there is provided a composite metal-oxide catalyst whose surface is modified by a metal hydroxide or a metal alkoxide and which is utilized in manufacturing a fatty acid ester of polyoxyalkylene alkyl ether represented by the following formula (I), through the reaction between a fatty acid alkyl ester and an alkylene oxide.

$$R_1\overset{O}{\overset{\|}{C}}(OR_2)_nOR_3 \tag{I}$$

wherein each of $R_1$ and $R_3$ independently represents an alkyl group or an alkenyl group, $R_2$ represents an alkylene group, and n is a positive number.

Still further, according to the present invention, there is provided a fatty acid ester of polyoxyalkylene alkyl ether represented by the following formula (I) and having an adduct distribution satisfying the following formula (A):

$$R_1\overset{O}{\overset{\|}{C}}(OR_2)_nOR_3 \tag{I}$$

wherein each of $R_1$ and $R_3$ independently represents an alkyl group or an alkenyl group, $R_2$ represents an alkylene group, and n is a positive number.

$$\sum_{i=n_{max}-2}^{i=n_{max}+2} Yi \geq 50 \tag{A}$$

wherein $n_{max}$ denotes a molar number of added alkylene oxide in an adduct accounting for a maximum proportion by weight in a total adduct, and Yi denotes a proportion by weight of an adduct having an i moles of added alkylene oxide to a total weight of an adduct.

BRIEF DESCRIPTION OF THE DRAWINGS

FIG. 1 is a graph showing a ethylene oxide adduct distribution of a fatty acid ester of polyoxyethylene alkyl ether in Example 1;

FIG. 2 is a graph showing ethylene oxide adduct distributions of fatty acid esters of polyoxyethylene alkyl ethers in Example 2 and Comparative Example 1;

DETAILED DESCRIPTION OF THE PREFERRED EMBODIMENTS

Figure 3:
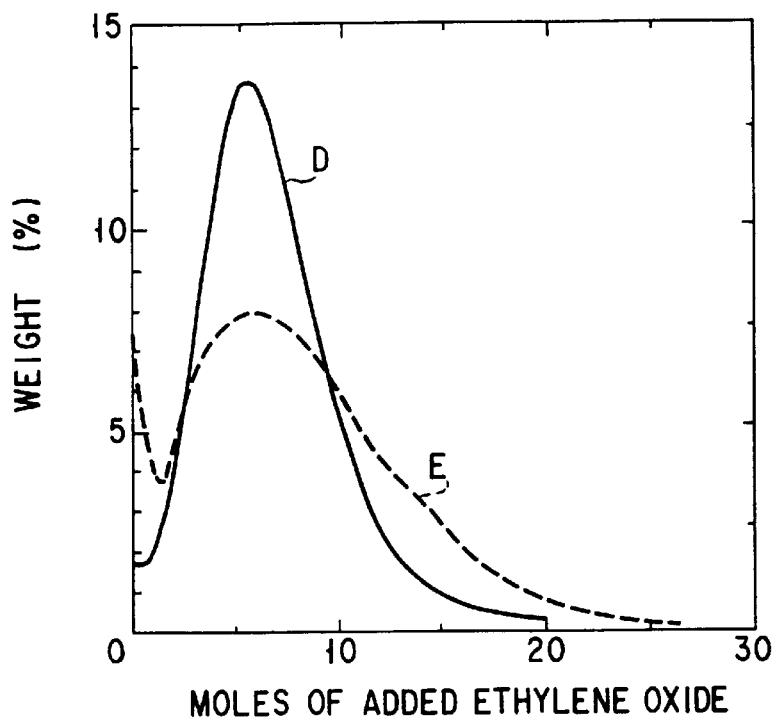
FIG. 3 is a graph showing ethylene oxide adduct distributions of fatty acid esters of polyoxyethylene alkyl ethers in Example 3 and Comparative Example 2.

The present inventors have conducted intensive studies with the view toward attaining the objects of the present invention. As a result, they found that active acidic points densely present on the surface of the aforementioned composite metal-oxide catalysts contribute to widening an alkylene oxide adduct distribution of the product. Further, they found that the composite metal-oxide catalysts can be modified if the active acidic points densely present on the surface of the composite metal-oxide catalysts are selectively partial-poisoned by a metal hydroxide or a metal alkoxide. Based on the above findings, they have accomplished the present invention.

More specifically, the method of manufacturing a fatty acid ester of polyoxyalkylene alkyl ether according to the present invention comprises a step of reacting a fatty acid alkyl ester with an alkylene oxide in the presence of an composite metal-oxide catalyst whose surface is modified by a metal hydroxide or a metal alkoxide. Owing to this method, it is possible to obtain a fatty acid ester of polyoxyalkylene alkyl ether represented by the following formula (I), having a narrow alkylene oxide adduct distribution accompanied with a small amount of a remaining unreactive fatty acid alkyl ester.

$$R_1\overset{O}{\overset{\|}{C}}(OR_2)_nOR_3 \tag{I}$$

wherein each of $R_1$ and $R_3$ independently represents an alkyl group or an alkenyl group, $R_2$ represents an alkylene group, and n is a positive number.

In the fatty acid alkyl ester ($R_1COOR_3$) used as a starting material of the present invention, $R_1$ preferably has 3 to 40 carbon atoms, and more preferably 6 to 22. $R_3$ preferably has 1 to 30 carbon atoms, and more preferably 1 to 4.

The alkyl group defined in the present invention includes also a group having a double bond in a carbon chain thereof (e.g. the so-called alkenyl group).

It is preferable that the alkylene oxide which is addition-polymerized to a fatty acid alkyl ester have 2 to 8 carbon atoms (the carbon number of $R_2$ is 2 to 8), and it is particularly preferable that ethylene oxide or propylene oxide having 2 to 3 carbon atoms be used.

The fatty acid alkyl ester and the alkylene oxide can be subjected to the reaction singly or in the form of mixture of two or more members.

The composite metal-oxides to be used in the present invention include: a magnesium oxide added with at least one metal ion selected from the group consisting of Al (aluminum), Ga (gallium), Zr (zirconium), In (indium), Ti (thallium), Co (cobalt), Sc (scandium), La (lanthanum) and Mn (manganese); a calcined hydrotalcite which may be converted to an Al—Mg series composite metal-oxide; and a calcined aluminum magnesium hydroxide (a coprecipitate of aluminum hydroxide and magnesium hydroxide).

The amount of the metal ion to be added to magnesium oxide is preferably 0.1 to 30 wt % based on the composite metal-oxide amount.

In the case where the calcined aluminum magnesium hydroxide is particularly used as the composite metal-oxide, a large catalytic surface can be obtained. Consequently, when an alkylene oxide is addition-polymerized to a fatty acid alkyl ester, the catalytic activity of the calcined aluminum magnesium hydroxide is higher than that of other composite metal-oxides.

Use of the aluminum magnesium hydroxide as the composite metal-oxide is industrially advantageous since the aluminum magnesium hydroxide makes it possible to efficiently promote the addition-polymerization reaction in a predetermined manner and to easily separate the catalyst from the reaction product after completion of the reaction.

A method of manufacturing the metal-ion added magnesium oxide is disclosed in Jpn. Pat. Appln. KOKAI Publication No. 1-164437. It is desirable that the metal-ion added magnesium oxide particles be manufactured by precipitating the metal-ion to be added from an aqueous solution containing the metal ion by the following methods:

1) Dipping method: MgO particles are added to an aqueous solution containing a metal ion to be added, such as an aqueous aluminum nitrate solution, mixed well, evaporated to dryness, pulverized and calcined, resulting in the catalyst particles.

2) Coprecipitation method: an aqueous magnesium salt solution, such as an aqueous magnesium nitrate solution, is mixed with an aqueous solution containing a metal-ion to be added, such as an aluminum nitrate solution, and a precipitating agent such as ammonia is added thereto, thereby coprecipitating magnesium and the metal ion to be added as hydroxides in the aqueous solution. These hydroxides are filtered, washed, dried, pulverized, and calcined to prepare catalyst particles.

3) Deposition method: an aqueous solution containing a metal-ion to be added to magnesium particles is added to a dispersion in which magnesium oxide particles are dispersed, and a hydroxide of the metal to be added is allowed to precipitate and deposit on the surface of magnesium oxide particles, subsequently filtrated, dried, and calcined.

In the case where a catalyst is manufactured by the precipitation method such as the coprecipitation or deposition method, undesired anions present in a catalyst slurry obtained after completion or precipitation treatment can be removed by an ion exchange resin, so that a washing step following the filtration can be omitted or simplified.

A hydrotalcite is represented by the following Formula (II). A natural hydrotalcite and a synthetic hydrotalcite can be used. A calcined hydrotalcite as an Al—Mg system composite metal-oxide can be obtained by calcining a hydrotalcite.

$$Mg_xAl_y(OH)_z(CO)_m \cdot nH_2O \tag{II}$$

wherein x, y, m and n each is a positive number.

The calcining temperature is preferably 400 to 800° C., and more preferably 450 to 700° C.

An aluminum magnesium hydroxide is represented by the following formula (III) and converted to an Al—Mg series composite metal-oxide by calcining.

$$nMgO \cdot Al_2O_3 \cdot mH_2O \tag{III}$$

wherein n and m, each is a positive number and n is preferably around 2.5.

The calcination temperature of the aluminum magnesium hydroxide is preferably 400 to 950° C., more preferably 400 to 700° C.

In the method of the present invention, a modified composite metal-oxide catalyst is obtained by reforming the surface of the composite metal-oxide with a metal hydroxide or a metal alkoxide, and then subjected to the reaction for obtaining a fatty acid ester of polyoxyalkylene alkyl ether.

A preferable metal hydroxide is an alkoxide of an alkali metal or an alkali earth metal, and a more preferable metal hydroxide is sodium hydroxide or potassium hydroxide.

A preferably metal alkoxide is an alkoxide of an alkali metal or an alkali earth metal, and a more preferable metal alkoxide is sodium alkoxide or potassium alkoxide.

The modified composite metal-oxide catalyst is manufactured by reforming a composite metal-oxide such as magnesium oxide added with a metal ion, a calcined hydrotalcite, or a calcined aluminum magnesium hydroxide, with a hydroxide of an alkali metal or an alkali earth metal, or an alkoxide of an alkali metal or an alkali earth metal and then subjected to the reaction as a catalyst. Alternatively, the modified composite metal-oxide catalyst is manufactured, in a reaction vessel for use alkoxylation, by steps of adding a composite metal-oxide, and a metal hydroxide or a metal alkoxide to a fatty acid alkyl ester which is used as a starting material for producing a fatty acid ester of polyoxyalkylene alkyl ether, mixing them, and reforming the composite metal-oxide in the fatty acid alkyl ester, and the composite metal-oxide catalyst thus-modified is reacted with an alkylene oxide.

The former method of reforming a composite metal-oxide is not particularly limited and it is preferable that the composite metal oxide be dried and calcined after it is sprayed with an aqueous solution or an alcohol solution of a metal hydroxide or a metal alkoxide.

In the latter method, the addition order of a composite metal-oxide, and a metal hydroxide or a metal alkoxide to the starting fatty acid alkyl ester is not particularly restricted. In this case, it is preferable that the metal hydroxide or the metal alkoxide by dissolved in a lower alcohol and then added to the fatty acid alkyl ester since acidic points on a catalyst surface can be more uniformly and selectively partial-poisoned.

The metal hydroxide or the metal alkoxide for use in reforming the composite metal-oxide is preferably used in an amount of 1 to 10 wt % based on the composite metal oxide amount.

The reaction of the present invention can be easily performed according to a customary operational procedure under normal reaction conditions. The reaction temperature employed is preferably 80 to 230° C., and more preferably 120 to 180° C. The reaction pressure employed is preferably 20 atm or less, and more preferably 2 to 8 atm, although it is dependent on the reaction temperature.

The amount of the catalyst varies depending on a molar ratio of the alkylene oxide to the fatty acid alkyl ester subjected to the reaction, and the catalyst is generally preferred to add in an amount of 0.1 to 20 wt % based on a fatty acid alkyl ester amount.

The reaction of the present invention is performed, for example, in the following procedure: a fatty acid alkyl ester and a modified catalyst are placed in an autoclave. After degassing and dehydration are effected, an alkylene oxide is introduced in the autoclave and the fatty acid alkyl ester is allowed to react with the alkylene oxide at predetermined temperature, under predetermined pressure conditions in an nitrogen atmosphere. After completion of the reaction, the resultant solution is cooled and the catalyst is separated by filtration.

Alternatively, the reaction of the present invention can be performed as follows: a fatty acid alkyl ester and a composite metal-oxide are placed in an autoclave. Subsequently, a metal hydroxide or a metal alkoxide for use in reforming a catalyst is added thereto and mixed well, and the composite metal-oxide is reformed in the autoclave. Thereafter, degassing and dehydrating are effected in the same manner as above. Subsequently, an alkylene oxide is addition-polymerized at a predetermined temperature under a predetermined pressure conditions in a nitrogen atmosphere. After completion of the reaction, the resultant reaction solution is cooled and the catalyst is separated by filtration.

As explained above, according to the present invention, owning to the use of the modified catalyst obtained by reforming the surface of a composite metal-oxide catalyst with a metal hydroxide or a metal alkoxide, it is possible to obtain a fatty acid ester of polyoxyalkylene alkyl ether having an alkylene oxide in an extremely narrow adduct distribution accompanied with a small amount of a remaining unreactive fatty acid alkyl ester, through one-step reaction between a fatty acid alkyl ester and an alkylene oxide.

An adduct distribution of fatty acid ester of polyoxyalkylene alkyl ether is expressed by the following equation.

$$\sum_{i=n_{max}-2}^{i=n_{max}+2} Yi$$

wherein $n_{max}$ denotes a molar number of added alkylene oxide in an adduct accounting for a maximum proportion by weight in a total adduct, and $Yi$ denotes a proportion by weight of an adduct having an i moles of added alkylene oxide to a total weight of an adduct.

The adduct distribution of fatty acid ester of olyoxyalkylene alkyl ether according to the present invention is 50% by weight or more, preferably 60% by weight or more in term of the above equation.

$$\sum_{i=n_{max}-2}^{i=n_{max}+2} Yi \geq 50$$

preferably, $$\sum_{i=n_{max}-2}^{i=n_{max}+2} Yi \geq 60$$

The amount of unreacted material contained in the fatty acid ester of polyoxyalkylene alkyl ether according to the present invention is as low as 5% by weight or less.

The fatty acid ester of polyoxyalkylene alkyl ether obtained by the method of the present invention, can be advantageously used for base materials of household cleaning agents and cosmetics, and base materials of cleaning agents in the chemical industry since odor derived from the unreacted fatty acid alkyl ester is weak and the fatty acid ester of polyoxyalkylene alkyl ether having a desired average alkylene oxide adduct number can be obtained in a large effective amount.

Hereinbelow, the present invention will be described in detail by way of Examples.

EXAMPLE 1

An aqueous solution obtained by dissolving 30 g of aluminum nitrate in 87 g of water was added dropwise to a dispersion obtained by dispersing 70 g of MgO in 525 g of water and aged for 30 minutes to prepare a slurry. To this slurry, 263 cc of a strong-basic ion exchange resin (trade name:SA-20A available from Mitsubishi Kagaku Corp.) was added after being converted to an OH type resin by pretreatment. Ion exchange was effected by stirring the mixture at room temperature for 1 hour. Consequently, $NO_3^-$ was removed from the slurry. After completion of ion exchange, the ion exchange resin was separated from the slurry by means of a screen having a mesh size of 300 μm. The resultant slurry was spray-dried, calcined for one hour at 600° C., resulting in a composite metal-oxide powder, namely, an Al-ion added MgO.

The composite metal-oxide powder was dried while 670 g of a 0.15 wt % methanol solution of NaOH was sprayed thereto, and further dried for 10 hours at 100° C. As a result, a modified catalyst A was obtained 12 g of the modified catalyst A thus obtained and 440 g of methyl laurate were placed in an autoclave. After air inside the autoclave was displaced with nitrogen, the mixture in the autoclave was heated under stirring. Subsequently, while the temperature was maintained at 180° C. and a pressure at 3 atm, a reaction with methyl laurate was carried out by introducing 543 g of ethylene oxide into the autoclave. After completion of the reaction, the resultant solution was cooled to 70° C. and filtrated to separate the catalyst.

The ethylene oxide adduct distribution of polyoxyethylene methyl ether laurate in the aforementioned manner is shown by a curve A of FIG. 1. As shown by the curve A of FIG. 1, the polyoxyethylene methyl ether laurate has a maximum peak value in an amount as high as 13.0 wt %. In other words, the ethylene oxide adduct distribution is narrow. The amount of remaining unreacted methyl laurate was as low as 3.5 wt %.

EXAMPLE 2

In an autoclave were placed 22 g of the composite metal-oxide obtained in the same manner as in Example 1 and 440 g of methyl laurate. Further, 1 g of a 28 wt % methanol solution of sodium methoxide was added thereto and the composite metal-oxide was modified in the autoclave.

After nitrogen purge and raising temperature were performed in the same manner as in Example 1, the reaction was carried out by introducing 543 g of ethylene oxide into the autoclave.

The ethylene oxide adduct distribution of polyoxyethylene methyl ether laurate is shown by a curve B of FIG. 2. As shown by the curve B of FIG. 2, the polyoxyethylene methyl ether laurate has a maximum peak value in an amount as high as 12.9 wt %. In other words, the ethylene oxide adduct distribution is narrow. The amount of remaining unreacted methyl laurate was as low as 2.9 wt %.

COMPARATIVE EXAMPLE 1

In an autoclave were placed 22 g of a composite metal-oxide (not yet modified) obtained in the same manner as in Example 1 and 440 g of methyl laurate. After the nitrogen purge and raising temperature were performed in the same manner as in Example 1, the reaction was performed by introducing 543 g of ethylene oxide.

The ethylene oxide adduct distribution of polyoxyethylene methyl ether laurate is shown by a curve C of FIG. 2. As shown by the curve C of FIG. 2, the polyoxyethylene methyl ether laurate has a maximum peak value in an amount as low as 7.2 wt %. In other words, the ethylene oxide adduct distribution is broad. The amount of remaining unreactive methyl laurate was as high as 8.5 wt %.

EXAMPLE 3

To an autoclave were added 440 g of methyl laurate, 11 g of a composite metal oxide obtained by calcining a hydrotalcite represented by a chemical formula: $Mg_6Al_2(OH)_{16}CO_3 \cdot 4H_2O$ for 1 hour at 500° C., and 3.5 g of a 5 wt % methanol solution of sodium hydroxide. The composite metal-oxide was modified in the autoclave. After the nitrogen purge and raising temperature were performed in the same manner as in Example 1, the reaction were performed by introducing 543 g of ethylene oxide. A catalytic activity (a rate of ethylene oxide addition per unit amount of catalyst) was 1.0 g EO/g(catalyst)/min.

The ethylene oxide adduct distribution of polyoxyethylene methyl ether laurate is shown by a curve D of FIG. 3. As shown by the curve D of FIG. 3, the polyoxyethylene methyl ether laurate has a maximum peak value in an amount as high as 13.9 wt %. In other words, the ethylene oxide adduct distribution is narrow. The amount of remaining unreacted methyl laurate was as low as 1.8 wt %.

COMPARATIVE EXAMPLE 2

Using a catalyst consisting of a composite metal-oxide which has not yet modified with the methanol solution of sodium hydroxide used in Example 3, the reaction between methyl laurate and ethylene oxide was performed in the same manner as in Example 3. A catalytic activity (a rate of ethylene oxide addition per unit amount of catalyst) was 3.2 g EO/g(catalyst)/min.

The ethylene oxide adduct distribution of polyoxyethylene methyl ether laurate is shown by a curve E of FIG. 3.

As shown by the curve E of FIG. 3, polyoxyethylene methyl ether laurate has a maximum peak value in an amount as low as 7.9 wt %. In other words, the ethylene oxide adduct distribution is broad. The amount of remaining unreactive methyl laurate was as high as 7.8 wt %.

In addition, the adduct distribution $$\sum_{i=n_{max}-2}^{i=n_{max}+2} Yi \text{ of the reaction product obtained was 40 wt\%.}$$

the reaction product obtained was 40 wt %.

EXAMPLE 4

To an autoclave were added 440 g of methyl oleate, 11 g of the composite metal-oxide obtained by calcining a hydrotalcite represented by a chemical formula: $Mg_{4.5}Al_2(OH)_{13}CO_3 \cdot 3.5H_2O$ for 1 hour at 600° C., and 1.7 g of a 10 wt % ethanol solution of magnesium ethoxide. After the nitrogen purge and raising temperature were performed in the same manner as in Example 1, the reaction with methyl oleate was performed by introducing 655 g of ethylene oxide.

The ethylene oxide adduct distribution of polyoxyethylene methyl ether oleate has a maximum peak value in an amount as high as 12.1 wt %. In other words, the ethylene oxide adduct distribution is narrow. The amount of remaining unreacted methyl oleate was as low as 1.2 wt %.

EXAMPLE 5

The same procedure as in Example 1 was employed to obtain a composite metal-oxide powder, namely, Ga-ion added MgO, except that 27 g of gallium nitrate was used instead of aluminum nitrate (30 g). To the composite metal-oxide powder, 2.5 g of a.28 wt % methanol solution of sodium methoxide was added. The mixture was dried to obtain a modified catalyst B.

23 g of the modified catalyst B thus obtained and 469 g of ethyl laurate were placed in an autoclave. After the nitrogen purge and raising temperature were performed in the same manner as in Example 1, the reaction with ethyl laurate was performed by introducing 543 g of ethylene oxide.

The ethylene oxide adduct distribution of polyoxyethylene ethyl ether laurate has a maximum peak value in an amount as high as 11.0 wt %. In other words, the ethylene oxide adduct distribution is narrow. The amount of remaining unreacted methyl laurate was as low as 4.7 wt %.

EXAMPLE 6

To an autoclave were added 440 g of methyl laurate, 1.5 g of the composite metal-oxide obtained by calcining an aluminum magnesium hydroxide (trade name: KYOWAAD 300CY, available from Kyowa Kagaku Kogyo) represented by a chemical formula: $2.5MgO \cdot Al_2O_3 \cdot nH_2O$ for 1 hour at 500° C. under a nitrogen flow, and 0.6 g of a 10 wt % methanol solution of potassium hydroxide. The composite metal-oxide was modified in the autoclave.

After the nitrogen purge and raising temperature were performed in the same manner as in Example 1, the reaction with methyl laurate was performed by introducing 543 g of ethylene oxide. A catalytic activity (a rate of ethylene oxide addition per unit amount of catalyst) was 3.2 g EO/g (catalyst)/min.

Figure 4:
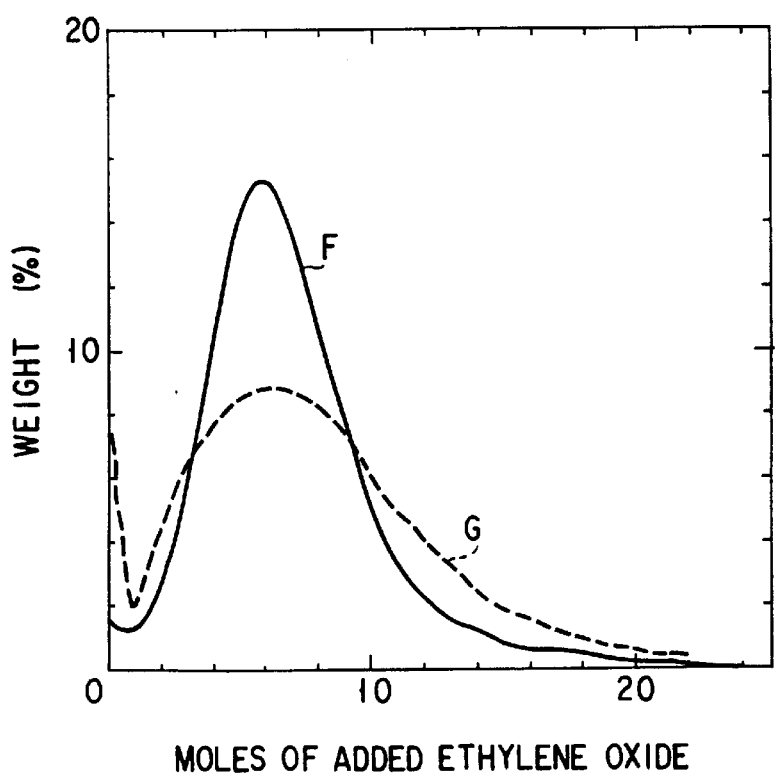
FIG. 4 is a graph showing an ethylene oxide adduct distributions of fatty acid esters of polyoxyethylene alkyl ethers in Example 6 and Comparative Example 3.

The ethylene oxide adduct distribution of polyoxyethylene methyl ether laurate is shown by a curve F of FIG. 4.

As shown by the curve F of FIG. 4, polyoxyethylene methyl ether laurate has a maximum peak value in an amount as high as 15.8 wt %. In other words, the ethylene oxide adduct distribution is narrow. The amount of remaining unreacted methyl laurate was as low as 1.7 wt %.

EXAMPLE 7

The same procedure as in Example 6 was employed to modify a composite metal-oxide except that 1.6 g of a 5 wt % methanol solution of potassium hydroxide was used.

After the nitrogen purge and raising temperature were performed in the same manner as in Example 1, the reaction with methyl laurate was performed by introducing 543 g of ethylene oxide. A catalytic activity (a rate of ethylene oxide addition per unit amount of catalyst) was 2.2 g EO/g (catalyst)/min.

Figure 5:
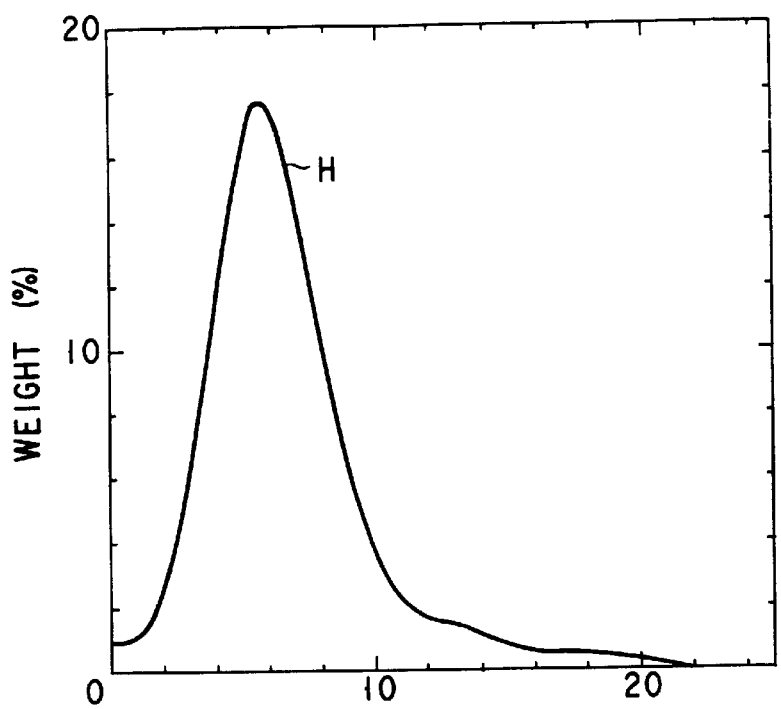
FIG. 5 is a graph showing an ethylene oxide adduct distribution of a fatty acid ester of polyoxyethylene alkyl ether in Example 7.

The ethylene oxide adduct distribution of polyoxyethylene methyl ether laurate is shown by a curve H of FIG. 5.

As shown by the curve H of FIG. 5, polyoxyethylene methyl ether laurate has a maximum peak value in an amount as high as 18.0 wt %. In other words, the ethylene oxide adduct distribution is narrow. The amount of remaining unreacted methyl laurate was as low as 1.0 wt %.

In addition, the adduct distribution $$\sum_{i=n_{max}-2}^{i=n_{max}+2} Yi \text{ of the reaction product obtained was 73 wt\%.}$$

the reaction product obtained was 73 wt %.

COMPARATIVE EXAMPLE 3

Using a catalyst consisting of a composite metal-oxide which has not yet modified with the methanol solution of potassium hydroxide used in Example 6, the reaction between methyl laurate and ethylene oxide was performed in the same manner as in Example 6. A catalytic activity (a rate of ethylene oxide addition per unit amount of catalyst) was 10.0 g EO/g(catalyst)/min.

The ethylene oxide adduct distribution of polyoxyethylene methyl ether laurate is shown by a curve G of FIG. 4.

As shown by the curve G of FIG. 4, polyoxyethylene methyl ether laurate has a maximum peak value in an amount as low as 8.9 wt %. In other words, the ethylene oxide adduct distribution is board. The amount of remaining unreacted methyl laurate was as high as 7.3 wt %.

EXAMPLE 8

To an autoclave were added 240 g of methyl laurate, 1.5 g of the composite metal-oxide obtained by calcining an aluminum magnesium hydroxide (trade name: KYOWAAD 300CY, available from Kyowa Kagaku Kogyo) represented by a chemical formula: $2.5\text{MgO}\cdot\text{Al}_2\text{O}_3\cdot n\text{H}_2\text{O}$ for 1 hour at 600° C. under a nitrogen flow, and 2.0 ml of a 0.5 N ethanol solution of potassium hydroxide. The composite metal-oxide was modified in the autoclave.

After the nitrogen purge and raising temperature were performed in the same manner as in Example 1, the reaction with methyl laurate was performed by introducing 743 g of ethylene oxide.

Figure 6:
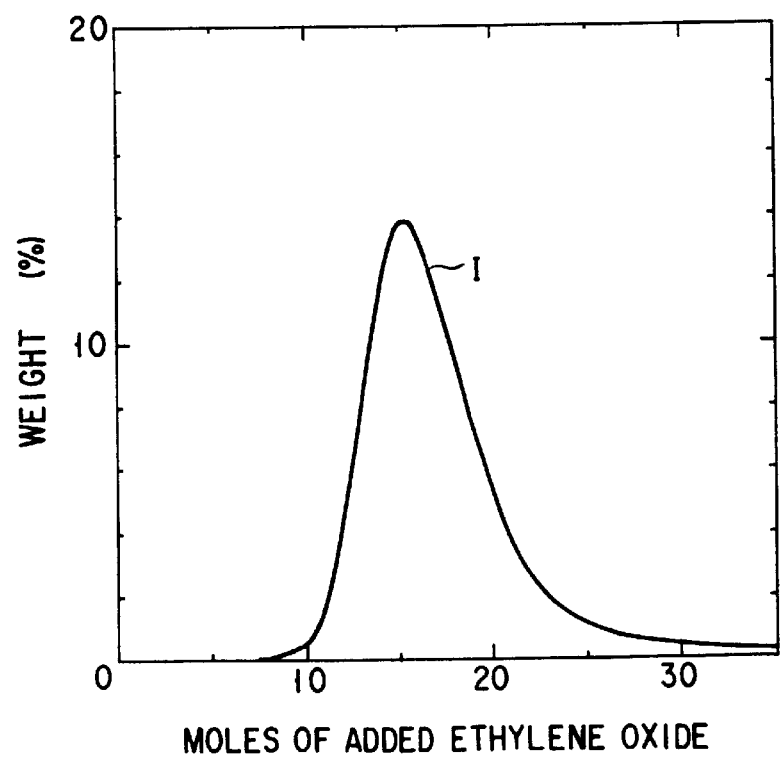
FIG. 6 is a graph showing an ethylene oxide adduct distribution of a fatty acid ester of polyoxyethylene alkyl ether in Example 8.

The ethylene oxide adduct distribution of polyoxyethylene methyl ether laurate is shown by a curve I of FIG. 6.

As shown by the curve I of FIG. 6, polyoxyethylene methyl ether laurate has a maximum peak value in an amount as high as 14.2 wt %. In other words, the ethylene oxide adduct distribution is narrow. No unreacted methyl laurate was remained.

In addition, the adduct distribution $$\sum_{i=n_{\max}-2}^{i=n_{\max}+2} Yi \text{ of the reaction product obtained was 65 wt\%.}$$

the reaction product obtained was 65 wt %.

EXAMPLE 9

To an autoclave were added 482 g of methyl oleate, 1.6 g of the composite metal-oxide obtained by calcining an aluminum magnesium hydroxide (trade name: KYOWAAD 300CY, available from Kyowa Kagaku Kogyo) represented by a chemical formula: $2.5\text{MgO}\cdot\text{Al}_2\text{O}_3\cdot n\text{H}_2\text{O}$ for 1 hour at 500° C. under a nitrogen flow, and 0.6 g of a 10 wt % methanol solution of potassium hydroxide. The composite metal-oxide was modified in the autoclave.

After the nitrogen purge and raising temperature were performed in the same manner as in Example 1, the reaction with methyl oleate was performed by introducing 501 g of ethylene oxide.

The polyoxyethylene methyl ether laurate thus obtained has a maximum peak value in an amount as high as 15.5 wt %. In other words, the ethylene oxide adduct distribution is narrow. The amount of remaining unreacted methyl oleate was as low as 3.5 wt %.

EXAMPLE 10

To an autoclave were added 440 g of methyl laurate, 11 g of the composite metal-oxide obtained by calcining an aluminum magnesium hydroxide (trade name: KYOWAAD 300CY, available from Kyowa Kagaku Kogyo) represented by a chemical formula: $\text{Mg}_{4.5}\text{Al}_2(\text{OH})_{13}\text{CO}_3\cdot 3.5\text{H}_2\text{O}$ for 1 hour at 500° C. under a nitrogen flow, and 4.4 g of a 10 wt % methanol solution of potassium hydroxide. The composite metal-oxide was modified in the autoclave.

After the nitrogen purge and raising temperature were performed in the same manner as in Example 1, the reaction with methyl laurate was performed by introducing 543 g of ethylene oxide.

The polyoxyethylene methyl ether laurate thus obtained has a maximum peak value in an amount as high as 13.0 wt %. In other words, the ethylene oxide adduct distribution is narrow. The amount of remaining unreacted methyl laurate was as low as 2.8 wt %.

EXAMPLE 11

The reaction was carried out in the same manner as in Example 9 except that 644 g of ethylene oxide was used.

The polyoxyethylene methyl ether oleate thus obtained has a maximum peak value in an amount as high as 17.7 wt %. The amount of remaining unreacted methyl oleate was 0 wt %. In addition, the adduct distribution $$\sum_{i=n_{\max}-2}^{i=n_{\max}+2} Yi \text{ of the reaction product obtained was 70 wt\%.}$$

COMPARATIVE EXAMPLE 4

The reaction was carried out in the same manner as Example 11 except that a composite metal-oxide catalyst not modified by a methanol solution of potassium hydroxide, and 482 g of methyl oleate, and 716 g of ethylene oxide were used.

The polyoxyethylene methyl ether oleate thus obtained has a maximum peak value in an amount as high as 5.8 wt %. The amount of remaining unreacted methyl oleate was 4 wt %. In addition, the adduct distribution $$\sum_{i=n_{\max}-2}^{i=n_{\max}+2} Yi \text{ of the reaction product obtained was 26 wt\%.}$$

EXAMPLE 12

The ethylene oxide adducts obtained in the Examples and Comparative Examples were tested for foaming property. The results are shown in Table 1. The foaming property was evaluated in terms of the initial foaming property, in accordance with a Ross-Miles method (0.1 wt %, 25° C.).

TABLE 1

| | Foaming Property | | |
|---|---|---|---|
| Test Sample | Alkyl-chain Length | Average EO-chain Length | Foaming Property (mm) |
| Example 7 | $C_{12}$ | 6 | 73 |
| Example 8 | $C_{12}$ | 15 | 113 |
| Example 11 | $C_{18:1}$ | 9 | 33 |
| Comparative Example 2 | $C_{12}$ | 6 | 60 |
| Comparative Example 4 | $C_{12}$ | 15 | 25 |

As is apparent form the results above, the foaming properties of the test samples (Examples 7, 8, 11) of the present invention are satisfactory in comparison with the conventional test samples (Comparative Examples 2, 4). It is thus demonstrated that the products of the present invention have excellent properties as a cleaning agent.

What is claimed is:

1. A fatty acid ester of polyoxyalkylene alkyl ether represented by the following formula (I):

(I)

wherein $R_1$ represents at least one member selected from the group consisting of an alkyl group and an alkenyl group each having 3 to 40 carbon atoms, $R_2$ represents an alkylene group having 2 to 8 carbon atoms, $R_3$ represents at least one member selected from the group consisting of an alkyl group and an alkenyl group each having 1 to 30 carbon atoms, and n is a positive number; and having an adduct distribution satisfying the following formula (A)

$$\sum_{i=n_{max}-2}^{i=n_{max}+2} Yi \geq 50 \tag{A}$$

wherein $n_{max}$ denotes a molar number of added alkylene oxide in an adduct accounting for a maximum proportion by weight in a total adduct, and Yi denotes a proportion by weight of an adduct having an i moles of added alkylene oxide to a total weight of an adduct.

2. The fatty acid ester of polyoxyalkylene alkyl ether according to claim 1, wherein a fatty acid alkyl ester moiety is an alkyl ester of a saturated or unsaturated fatty acid having a carbon number of 6 to 22.

3. The fatty acid ester of polyoxyalkylene alkyl ether according to claim 1, wherein a fatty acid alkyl ester moiety is an ester between a saturated or unsaturated fatty acid and an alkanol having a carbon number of 1 to 4.

4. The fatty acid ester of polyoxyalkylene alkyl ether according to claim 1, wherein said alkylene oxide is one selected from the group consisting ethylene oxide and propylene oxide.

5. The fatty acid ester of polyoxyalkylene alkyl ether according to claim 1, which contains a fatty acid alkyl ester in an amount of 5 wt % or less.

6. The fatty acid ester of polyoxyalkylene alkyl ether according to claim 1, which has an adduct distribution satisfying the following formula (B)

$$\sum_{i=n_{max}-2}^{i=n_{max}+2} Yi \geq 60 \tag{B}$$

7. The fatty acid ester of polyoxyalkylene alkyl ether according to claim 6, which contains a fatty acid alkyl ester in an amount of 5 wt % or less.

8. The fatty acid ester of polyoxyalkylene alkyl ether according to claim 1 obtained by reacting a fatty acid alkyl ester with an alkylene oxide.

* * * * *